US012758696B2

(12) United States Patent
Lindo et al.

(10) Patent No.: US 12,758,696 B2
(45) Date of Patent: Oct. 13, 2026

(54) AUTOMATED PERITONEAL DIALYSIS DEVICE, SYSTEM AND METHOD OF CUSTOMIZING DIALYSATE SOLUTIONS

(71) Applicant: Simergent LLC, Chicago, IL (US)

(72) Inventors: Steve J. Lindo, Chicago, IL (US); Richard A. Pendergraft, Norman, OK (US); Jacob Henderson, Oklahoma City, OK (US)

(73) Assignee: Simergent LLC, Palos Park, IL (US)

( * ) Notice: Subject to any disclaimer, the term of this patent is extended or adjusted under 35 U.S.C. 154(b) by 232 days.

(21) Appl. No.: 18/614,836

(22) Filed: Mar. 25, 2024

(65) Prior Publication Data

US 2024/0252730 A1 Aug. 1, 2024

Related U.S. Application Data

(62) Division of application No. 16/988,968, filed on Aug. 10, 2020, now Pat. No. 11,957,823.

(Continued)

(51) Int. Cl.

| | |
|---|---|
| ***A61M 1/28*** | (2006.01) |
| ***A61M 1/14*** | (2006.01) |
| ***A61M 1/16*** | (2006.01) |
| ***A61M 1/26*** | (2006.01) |
| *G01F 22/02* | (2006.01) |

(52) U.S. Cl.

CPC ............ *A61M 1/287* (2013.01); *A61M 1/155* (2022.05); *A61M 1/1565* (2022.05); *A61M 1/159* (2022.05); *A61M 1/1605* (2014.02); *A61M 1/1654* (2013.01); *A61M 1/1656* (2013.01); *A61M 1/267* (2014.02); *A61M 1/282* (2014.02); *A61M 1/285* (2013.01); *A61M 2205/121* (2013.01); *A61M 2205/125* (2013.01); *A61M 2205/128* (2013.01); *A61M 2205/52* (2013.01); *G01F 22/02* (2013.01)

(58) Field of Classification Search

CPC .... A61M 1/155; A61M 1/1565; A61M 1/159; A61M 1/1605; A61M 1/1654; A61M 1/1656; A61M 1/267; A61M 1/282; A61M 1/285; A61M 1/287; A61M 2205/121; A61M 2205/125; A61M 2205/128; A61M 2205/52; G01F 22/02

See application file for complete search history.

(56) References Cited

U.S. PATENT DOCUMENTS 4,668,400 A * 5/1987 Veech ................ A61M 1/1666 210/96.2
12,064,542 B2 * 8/2024 Musca .................. G16H 20/40

(Continued)

OTHER PUBLICATIONS

Wang et al., Kidney International, vol. 52 (1997), pp. 1609-1616.*

*Primary Examiner* — John Kim

(74) *Attorney, Agent, or Firm* — Stephen T. Scherrer; Monique A. Morneault; Scherrer Patent & Trademark Law, P.C.

(57) ABSTRACT

An automated peritoneal dialysis (APD) device, system and method is provided, which utilizes mechanisms to admix customized dialysate solutions from multiple sources, while maximizing volumetric accuracy. The present automated peritoneal dialysis (APD) device can accomplish these goals all within the convenience and comfort of the patient's home utilizing filtered tap water.

10 Claims, 8 Drawing Sheets

Related U.S. Application Data

(60) Provisional application No. 62/885,058, filed on Aug. 9, 2019.

(56) References Cited

U.S. PATENT DOCUMENTS

| | | | | |
|---|---|---|---|---|
| 2006/0037910 | A1* | 2/2006 | Shah | A61K 45/06<br>210/321.71 |
| 2018/0021501 | A1* | 1/2018 | Gerber | A61M 1/287<br>604/28 |
| 2018/0043076 | A1* | 2/2018 | Gerber | A61M 1/287 |
| 2018/0361048 | A1* | 12/2018 | Scarpaci | A61M 1/282 |

* cited by examiner

AUTOMATED PERITONEAL DIALYSIS DEVICE, SYSTEM AND METHOD OF CUSTOMIZING DIALYSATE SOLUTIONS

STATEMENT REGARDING FEDERALLY SPONSORED RESEARCH OR DEVELOPMENT

This invention was made with government support under R43 DK116436 awarded by the National Institutes of Health. The government has certain rights in the invention.

TECHNICAL FIELD

The present disclosure relates generally to automated peritoneal dialysis devices. More specifically, the present disclosure relates to providing an automated peritoneal dialysis (APD) device, system and method for use in in-home or on-site generation of customized peritoneal dialysis solution, also known as dialysate, by mixing sterile water with dialysate components which may come in either powdered or liquid form. The present disclosure further relates to an APD device incorporating a disposable fluid mixing cassette and tubing set for use in the peritoneal dialysis device and system, and a software support application for use in creating a customized peritoneal dialysis solution depending on patient specifications and requirements.

BACKGROUND

Peritoneal dialysis (PD) consists of a series of cycles of filling, dwelling, and draining dialysate solution into and out of a patient's peritoneal cavity in their lower abdomen for patients with Chronic Kidney Disease (CKD) or End Stage Renal Disease (ESRD). The solution is exchanged by connecting one or more dialysate solution bag(s) and associated disposable tubing to a transfer set with a shutoff valve, which in turn connects to a PD catheter surgically implanted in the patient's abdomen. Peritoneal dialysate solution contains dextrose, icodextrin (starch), or other solute molecules in sterile water to create an osmotic gradient which allows toxins and excess fluids in the bloodstream to transport through the peritoneal membrane's capillary walls and into the dialysate solution. Peritoneal dialysate solution also contains electrolytes to maintain patients' normal blood composition. Dextrose-based peritoneal dialysate solution is commercially available in different dextrose concentrations. Diffusion and osmosis occurs between the blood within the patient's peritoneal membrane capillaries and the solution dwelling in contact with that membrane, after having been filled from the APD device or via Continuous Ambulatory Peritoneal Dialysis (CAPD).

Conventional peritoneal dialysate consists of a single chamber bag with a low pH solution. It is well established that these solutions contain dextrose degradation products (GDPs), which can lead to the formation of advanced glycation end products (AGEs). All three of these factors—low pH, GDPs, and AGEs have been established as being bioincompatible to a patient's peritoneum, which can result in degradation of the peritoneal membrane and undesired changes in its transport characteristics over time. A storage challenge with conventional peritoneal dialysate in single-chamber bags is that bicarbonate cannot be used as the buffer, because it has the potential to react with calcium in the dialysate and form calcium-carbonate precipitates.

Some commercially available biocompatible peritoneal dialysate is manufactured in multi-chamber bags such that the dextrose and electrolyte solution is housed in one chamber as a very low-pH solution, which helps reduce the formation of GDPs, while one of the additional chamber(s) contains a buffer solution such that, when mixed together, the final solution is at or near the pH of a patient's blood, or approximately 7.4. The buffer typically contains bicarbonate, lactate, or a mixture of both. Because the calcium is stored in the dextrose-containing chamber, separated from the buffer, there is no risk for calcium-bicarbonate interaction during storage. Patients or caregivers must remember to break the seal between two-chamber bags before using the fluid for delivery to the patient.

PD therapy is performed either via gravity with dialysate bag(s) hung on a pole or elevated shelf, or with a device (cycler) to provide the motive fluid pressure/suction, also known as Automated Peritoneal Dialysis (APD). APD therapy is typically performed for 8-10 hours each night while the patient sleeps. Dialysate bags are typically hung at the beginning of therapy, and are typically removed after therapy completion. The patient and/or a family member or caregiver typically sets up the APD device, also known as a cycler, its associated disposable tubing set, and peritoneal dialysate bags each night before commencing therapy. These users are often asked to adjust prescription settings on the cycler's user interface, which may be difficult for some users to accomplish, given the complexity of certain APD therapy prescription settings. Users are also tasked with connecting different strength dextrose bags on different days, depending on the patient's fluid overload status.

Today, dialysate bags are shipped great distances, often from a single manufacturing site within a country or region, to intermediate warehouses, then shipped to PD patient's homes. Given that the majority of the dialysate weight consists of water, there is a great deal of expense associated with shipping this water all over the world, especially considering that most patients have a source of tap water in their homes.

Today, PD patients typically receive a 30-day supply of dialysate solutions from the manufacturer. This monthly shipment also often contains extra bags of multiple concentrations, which the patient may or may not use, to ensure that the patient will not run out of any concentration that he or she may use in a given month. This results in patients having 30 to 90+ boxes of dialysate which must be stored in their homes. Patients often store their dialysate in some combination of living room, bedroom, hallways, closets, and/or garages. Garage storage is discouraged because dialysate fluids are intended to be stored in an environment which avoids temperature extremes. Patients often lament the quantity and size of dialysate boxes that occupy their homes as an undesired byproduct of PD therapy.

Currently, dialysate bags are commercially available in only a single sodium concentration (132-134 mmol/l). Recent evidence suggests that low sodium dialysate solutions may provide cardiovascular benefits to hypertensive patients including lower blood pressure, fewer antihypertensive medications, and reduced volume load on the heart muscle as a result of reducing patients' fluid overload status. Given that the typical Western diet contains 3000-4500 mg/day of sodium while the recommended daily intake is only 1500 mg/day, there is a need to remove excess sodium from many patients' bloodstreams. It is estimated that up to 80% of dialysis patients have hypertension. Low sodium peritoneal dialysate solutions can remove excess sodium from the bloodstream via transperitoneal sodium removal, whereby sodium diffuses across the peritoneal membrane from the blood to the dialysate solution due to a large sodium concentration gradient between the two fluids.

A normal adult serum potassium level is 3.6 to 5.2 mmol/L. Current commercially available dialysate bags contain no potassium, despite the fact that some of the potassium in the patients' bloodstream may diffuse out of the bloodstream across the peritoneum and into the dialysate fluid during dialysis treatment. This may lead to hypokalemia, a potentially serious complication. Currently, 10-36% of PD patients suffer from hypokalemia. Additionally, it is well established that increasing serum potassium levels may reduce blood pressure for hypertensive patients. By reducing elevated blood pressure, an increase in potassium can reduce the risk of cardiovascular complications including heart attacks and strokes. There is significant potential benefit for PD dialysate solutions to have the option to include a variable dose of potassium to treat or prevent hypokalemia or hyperkalemia.

In addition, today, dialysate bags are often difficult to lift up to place them in the proper position required for therapy. Dialysate bag volumes may reach or exceed 5000-6000 ml, with corresponding weights of approximately 50-60 Newtons. These bags typically must be lifted from their original shipping container(s) (e.g. cardboard box) from approximately ground level to either approximately waist height for active pumping APD devices, or from ground level to 1.2-1.8 meters above ground level for gravity-based APD devices, in order to achieve the necessary head height required for appropriate therapeutic flow rates. Furthermore, the peritoneal dialysis patient population tends to skew on the older side, thus exacerbating these potential lifting difficulties. Lifting heavy dialysate bags may cause shoulder or back problems, may lead to the user losing balance and/or falling over. These same difficulties may be experienced by caregivers who may perform setup rather than the patients themselves. Additionally, patients and caregivers in certain regions in the globe and/or female patients may have smaller statures and may not have as much strength as others. Further, many PD patients also suffer from other comorbidities or illnesses such as diabetes mellitus, which may further reduce the patient's ability to lift heavy objects.

To date, there have been no commercially available APD cyclers which generate peritoneal dialysate solutions within the patients' homes, and no APD cyclers which admix customizable sodium, potassium, and/or dextrose concentrations tailored to each individualized patient's needs. Existing APD devices utilize pre-prepared sterile dialysate bags shipped to the patient's homes. As such, patients may be hesitant to choose PD as their renal replacement therapy modality because they may not want the burden of excessive dialysate box storage, or may not be able to physically lift the heavy 5-6 liter bags from the boxes stored in their homes onto, or within close proximity to, the cycler. Those patients may be forced to perform hemodialysis instead, which may not be their preferred dialysis modality.

Prior patents have discussed the generation of peritoneal dialysate by having the APD device mix the components in a syringe before delivering them to the patient. This requires an extra component, the syringe, in the disposable tubing set, as well as multiple delivery mechanisms with the capability to deliver fluids to/from a flexible pump chamber and to/from a syringe, adding unnecessary cost to the device and disposable set. They do not describe how to ensure that the tubing set remains free of a single dialysate component prior to deliver to the patient.

If the peritoneal dialysate components are generated onsite, it requires mixing sterile water with one or more concentrated solutions such that the final product will be at the desired final concentration of dextrose or other ingredient intended to produce an osmotic gradient. If these components are mixed in an admixing bag or compartment prior to delivery to the patient, and assuming that admixing bag has only one tube connecting it to the remainder of the disposable tubing set, then immediately following the delivery of the last solution component to the admixing bag, the tube leading to the bag will contain only one component of the dialysate solution. If the APD device were to then deliver fluid from the admixing bag to the patient, the first bolus of fluid delivered would be unsuitable for delivery to the patient, as its chemical composition would not contain the desired final concentration of dextrose. A patient could experience internal chemical burns if the pH of the fluid remaining in the tubing set were very low. Alternatively, the patient's peritoneal membrane could be exposed to more or less dextrose or electrolytes than desired, which could have negative therapeutic outcomes. Alternatively, a patient could lose important electrolytes from their blood if the fluid remaining in the tubing set were to consist of only sterile water and that fluid were delivered to the patient. These problems could be exacerbated if the patient were a pediatric patient such that the holdup volume of the tubing leading to the admixing bag were a significant percentage of the total per-cycle fill volume to be delivered to the patient. Other complications could include less effective therapeutic outcomes and/or longer therapy.

Accordingly, there is a need for an invention that addresses dialysate composition after mixing in an intermediate mixing compartment or bag, resulting in safe, efficient, and effective therapy. These same sodium limiting or potassium addition principals can be applied to peritoneal dialysis or hemodialysis.

SUMMARY

To meet the needs described above and others, the present disclosure provides multiple solutions to the problem of admixing customizable dialysate solutions to facilitate individualized medicine, reduce the burden of lifting heavy bags, promote sodium removal, promote potassium addition, and improve cardiovascular outcomes. Specifically, the present disclosure provides an improved automated peritoneal dialysis (APD) device and system which is ideal for in-home dialysis treatment.

To this end, in an embodiment of the present disclosure, a device for creating a customized peritoneal dialysis solution and administering peritoneal dialysis on a patient, is provided. The device comprises: a unit housing, a cassette housing disposed within the unit housing, a cassette contained within the cassette housing, at least one pump chamber formed within the cassette, a plurality of inlet ports and outlet ports connected to the cassette, the inlet ports and outlet ports fluidly connected to the at least one pump chamber, at least one valve for selectively sealing off and re-opening fluid communication between any one or more of the input ports and output ports and the at least one pump chamber, a plurality of inlet lines and outlet lines connected to the inlet ports and outlet ports, the inlet lines and outlet lines connected to a plurality of bags, vials, or other containers containing the desired liquid components for a dialysate solution, wherein the at least one pump chamber within the cassette is configured to withdraw and measure a volume of a selected quantity of liquid components from the source containers and deliver a selected volume of the chosen liquid to an admixing bag to allow the mixing together of selected quantities of the liquid components to provide a dialysis solution of a desired final formulation;

and, a pneumatic manifold contained within the unit housing and fluidly connected to the cassette housing, the pneumatic manifold including controls for opening and closing the valves and the at least one pump chambers for controlling the delivery of a selected volume of dialysate of a desired final formulation from the pump chambers to the patient.

In another embodiment of the present disclosure, a method for creating a customized peritoneal dialysis solution and administering the solution to a patient is provided. The method comprises the steps of providing a plurality of bags containing solution components for creating a dialysis solution, providing a unit device containing a fluid mixing cassette assembly having a plurality of inlet ports and outlet ports, connecting a plurality of lines to the inlet ports and the outlet ports of the cassette each to the respective bags of dialysate solution components, mixing a selected volume of each of the dialysate solution components withdrawn from the respective bag in the fluid mixing cassette assembly, creating a customized dialysate solution having a desired final composition, delivering the customized dialysate solution to a receptacle for administering to a patient.

In yet another embodiment, a method for determining an appropriate peritoneal dialysis prescription tailored to meet treatment needs of a patient is provided. The method comprises the steps of providing an input computing device, inputting patient health parameters into the computing device, using the computing device to calculate a concentration of electrolytes for the solution (pre-mixed and/or post-mixed concentration) based in the patient health parameters, inputting the calculated concentration of electrolytes into an automated peritoneal dialysis (APD) device, mixing the concentration of electrolytes in the APD device into a solution suitable for administration to the patient and, administering the solution to the patient.

In satisfaction of this and related objects, the present disclosure provides an improved automated peritoneal dialysis (APD) device which is unique in its design, manufacturability, and its capacity to serve as a peritoneal dialysis device in a cost-effective manner.

An object of the present disclosure is to provide an improved automated peritoneal dialysis device and system for use in an in-home setting.

Another object of the present disclosure is to provide an improved APD device and system, which allows delivery of any desired dextrose concentration from 1.0% to 4.5% in increments of 0.25% dextrose.

Another object of the present disclosure is to provide an improved APD device and system which allows delivery of any desired sodium concentration from 100 mEq/l to 170 mEq/l in increments of 10 mEq/l.

Another object of the present disclosure is to provide an improved APD device and system which allows delivery of any desired potassium concentration from 0 mEq/l to 6 mEq/l in increments of 0.5 mEq/l.

Another object of the present disclosure is to provide an improved APD device and system which allows for targeted sodium removal from or replacement into the patient's bloodstream.

Another object of the present disclosure is to provide an improved APD device and system which allows for targeted potassium removal from or replacement into the patient's bloodstream.

Another object of the present disclosure is to provide an improved APD device and system which allows delivery different dextrose concentrations during each fill cycle to limit the overall dextrose exposure to the peritoneal cavity (dextrose profiling).

Another object of the present disclosure is to provide an improved APD device and system which helps clinicians choose the dialysate dextrose concentration to automatically adjust for the loss of osmotic gradient when a lower sodium concentration is selected.

Another object of the present disclosure is to provide an improved APD device and system which helps clinicians choose the proper dialysate sodium concentration that will enable a programmable amount of sodium to be removed from the patient's bloodstream each day or each week.

Another object of the present disclosure is to provide an improved APD device and system which helps clinicians choose the proper dialysate potassium concentration that will enable a programmable amount of potassium to be added to the patient's bloodstream each day or each week.

Another advantage of the APD device and system of the present disclosure is that it saves dialysate shipping costs and associated environmental impact with the use of highly concentrated dialysate solutions.

Another advantage of the APD device and system of the present disclosure is that it uses commercially available hypertonic saline solution to reduce research and development costs and reduce the number of unique products a manufacturer, clinic, or hospital may have to carry.

Another advantage of the APD device and system of the present disclosure is that it uses commercially available potassium chloride solution, which may be dissolved in 0.9% sodium chloride solution and/or dextrose solution to reduce research and development costs and reduce the number of unique products a manufacturer, clinic, or hospital may have to carry.

Another advantage of the APD device and system of the present disclosure is that it can mix or agitate the contents of the admix bag prior to delivery to the patient so the patient is receiving the intended concentration and not a pre-mixed single source of fluid.

Another advantage of the APD device and system of the present disclosure is to provide improved volumetric measurement accuracy (measured volume delivered vs. actual delivered volume) versus traditional APD systems.

Another advantage of the APD device and system of present disclosure is to provide improved volumetric targeting accuracy (target volume to deliver vs. actual delivered volume) versus traditional APD systems.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION

The automated peritoneal dialysis (APD) device and system of the present disclosure, in the preferred embodiments, utilizes mechanisms to admix customized dialysate solutions from multiple sources, while maximizing volumetric accuracy. The present automated peritoneal dialysis (APD) device can accomplish these goals all within the convenience and comfort of the patient's home utilizing filtered tap water.

Figure 1:
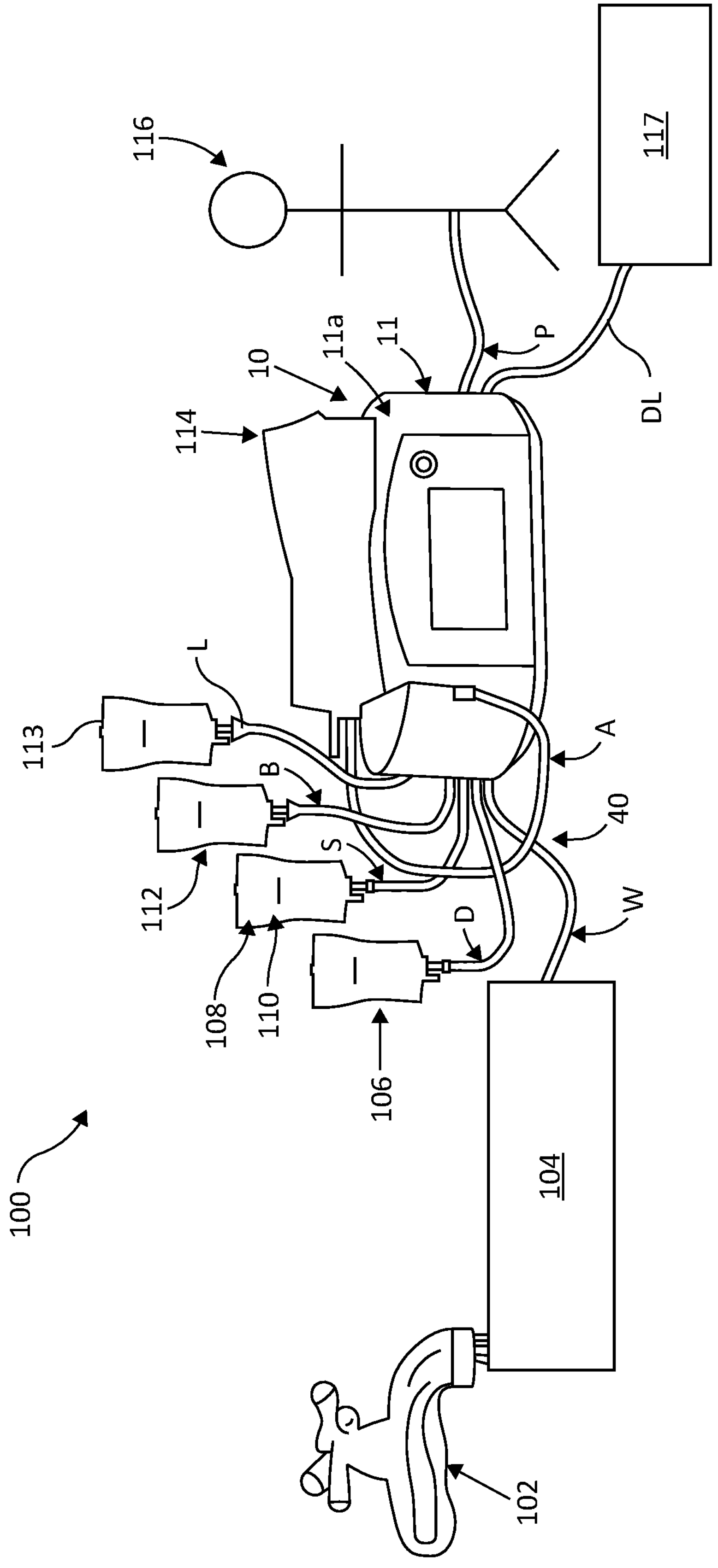
FIG. 1 illustrates an automated peritoneal dialysis (APD) system utilizing the automated peritoneal dialysis (APD) device of the present disclosure.

FIG. 1 illustrates an embodiment of an automated peritoneal dialysis (APD) system 100 utilizing the automated peritoneal dialysis (APD) device 10 of the present disclosure. An advantage of the present system 100 and device 10 is that it allows for customization of solutions for use in peritoneal dialysis, which may include but are not limited to, one or two dextrose concentrate solutions, a buffer solution, a sodium solution, a potassium solution, sterile water, or a Last Fill solution which may include icodextrin. Selection of the appropriate solutions will depend on the specific patient requirements and treatment goals.

As shown in in FIG. 1, use of the present APD system 100 begins with plugging the APD device 10 to an electrical source (not shown) and a source 102 of tap water from the patient's home being routed into a water purifier 104. The water purifier 104 filters and sterilizes the incoming water and routes clean injection-quality water to the fluid delivery components, including a disposable cassette 30 housed within the APD device housing 11 via the water line W on the disposable tubing set 40. The water filtration device may route heated water to the disposable set to facilitate tubing set reuse. A plurality of bags containing appropriate solutions to create a customized dialysate solution are provided. As with the water line W, all of the solution containing bags are connected to the fluid delivery component within the APD device housing 11. For example, a dextrose concentrate bag 106 is connected through the D line (up to 2 dextrose sources may be connected, although only one is shown here.) A sodium solution bag 108, which consists of normal saline, hypertonic saline, or any other electrolyte, is shown connecting to the disposable tubing line S. Optionally, depending on treatment goals, a potassium solution bag 110 may also be used. A buffer solution bag 112 connects through disposable tubing line B. A last fill bag 113, which may contain a dextrose solution or icodextrin solution, is shown through tubing line L. Finally, before patient administration, an admix bag 114 is connected to the disposable tubing line A. The admix bag 114 may be placed on the top surface 11*a* of the APD device housing unit 11, wherein the solution contained therein is ideally heated to approximately human body temperature prior to filling the patient 116. The patient's spent effluent is drained through tubing line DL into a drain container, tub, floor drain or toilet 117. The APD device 10 may further known operating components including: a user interface with a color touch screen panel and a Power/Stop button with power indicator LED. The patient 116 shown on the right is connected to the device 10 via the disposable tubing Patient Line P.

Figure 2:
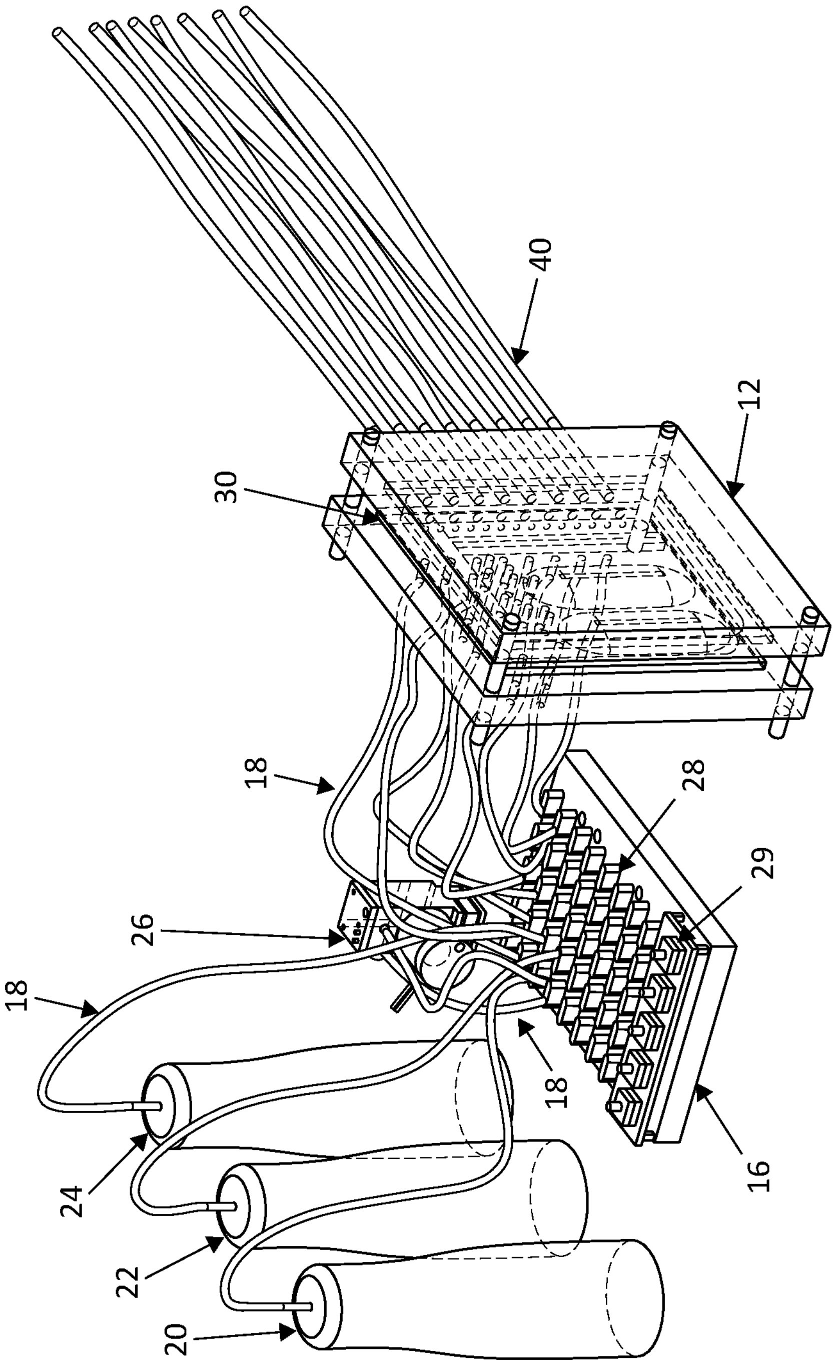
FIG. 2 illustrates the disposable cassette and pneumatic components of the automated peritoneal dialysis (APD) device of the present disclosure.

FIG. 2 illustrates the components of the APD device 10 of the system 100 that are contained within device housing 11 (FIG. 1). The components of the APD device 10 generally include fluid delivery components in a cassette housing 12 and pneumatic and electronic components in the pneumatic manifold 16. The APD device 10 includes a cassette housing 12 containing a disposable cassette 30, which operates to admix customized dialysate solutions from multiple sources. The cassette housing 12 includes a pair of flexible membrane gaskets 13 between the cassette and the cassette housing, one on either side of the cassette, to prevent air leaks. As will be described, the cassette 30 includes at least one pump chamber 32 having a plurality of valves 31 referred to as volcano valves. A plurality of fluid lines 40 are shown running out the right side of the cassette 30, with each fluid line connecting to the appropriate solution bag, including the dextrose concentrate bag 106, sodium or potassium solution bag 108, buffer solution bag 112, water purifier source 104, etc., as previously described. FIG. 2 depicts a 9-line cassette, but an 8-line or fewer line cassette could be envisioned if certain lines were omitted, such as consolidating the two dextrose lines into one or omitting the sodium/potassium solution line and/or buffer line.

As further illustrated in FIG. 2, a pneumatic manifold 16 connects to the back of the cassette housing 12 (specifically to the valves 31 and pump chambers 32) through a plurality of pneumatic tubing 18. The pneumatic manifold 16 also connects to three air accumulators—a High Positive Tank 20, a Low Positive Tank 22, and a Negative Tank 24, which provide the air regulated through an air pump 26 with positive and vacuum capabilities to the manifold 16. The pneumatic manifold 16 contains solenoid valves 28 and pressure transducers 29, which operate to control and regulate the air flow from the air accumulators 20, 22, 24 through the pneumatic tubing 18 to the cassette housing 12 for the mixing operation of the disposable cassette 30. It may also contain temperature sensors, which may be separate or integrated within the pressure transducers to improve volumetric accuracy.

Figure 3:
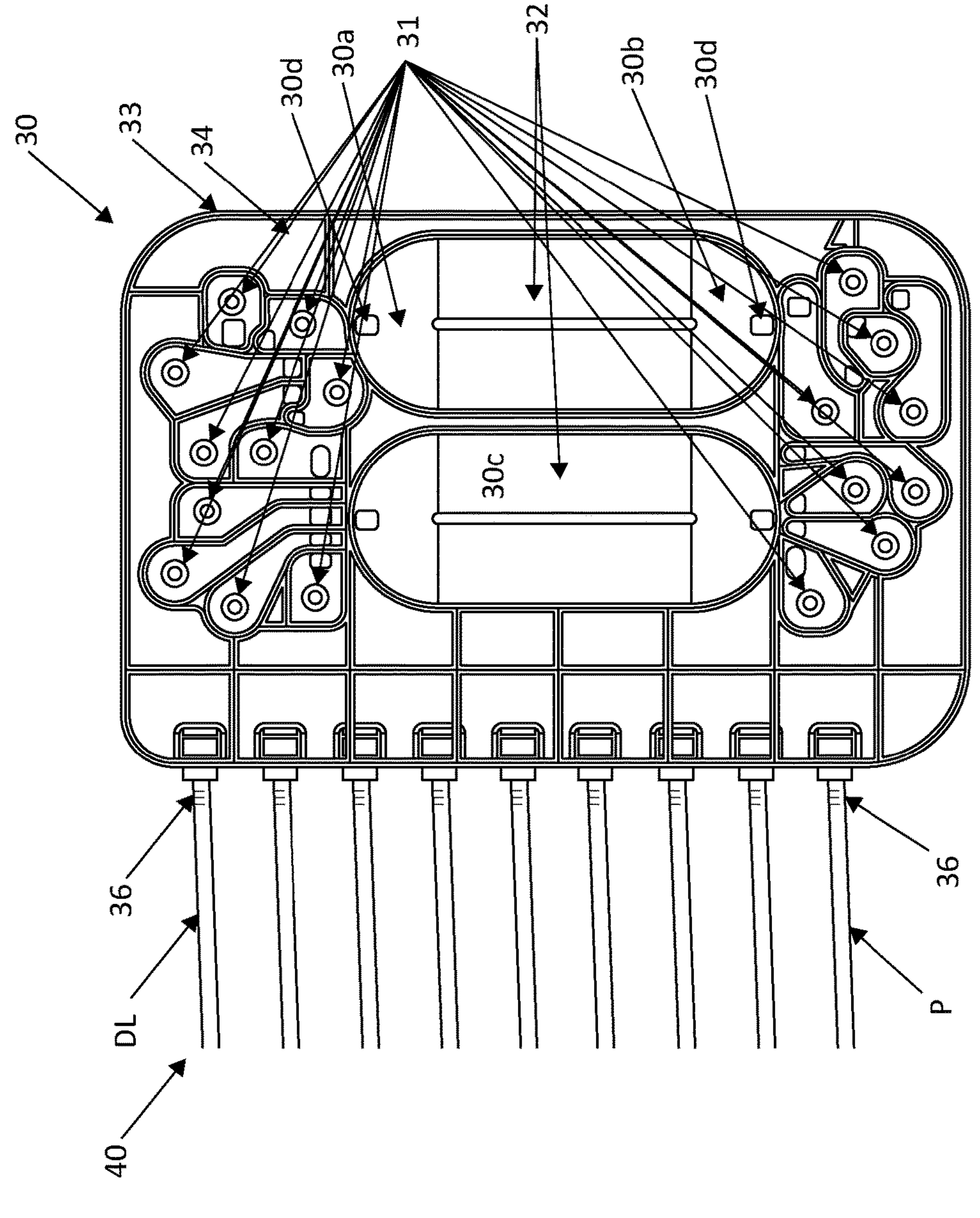
FIG. 3 illustrates an embodiment of a disposable cassette useful in the automated peritoneal dialysis (APD) device of the present disclosure.

FIG. 3 illustrates the details of the disposable cassette 30 and its pump chambers 32. In this embodiment, two pump chambers 32 are shown; however, it should be understood that any number of pump chambers may be utilized in the cassette. For example, optionally, three or four pump chambers may be incorporated into the cassette, which are smaller in size than the two pump chambers, such that smaller volumes may be targeted to improve targeting accuracy. Additionally, this particular cassette 30 embodiment shows 9 fluid inlet/outlet ports 36, but an 8-port or 7-port version would be very similar, with 2 fewer volcano valves (one to each pump chamber) for each inlet/outlet port removed.

The pump chambers 32 are formed by a concave rigid cassette body 33 covered on both sides by flexible plastic sheeting 34. When appropriate pneumatic pressure from the pneumatic manifold 16 is applied to the flexible plastic sheeting 34, the fluid within the pump chamber 32 is forced out as the sheeting bends to approach or touch the hard plastic pump chamber's concave base 33. Fluid is drawn into the pump chamber 32 by applying negative (vacuum) pressure to the outer surface of the flexible sheeting 34.

The disposable cassette 30 acts like a two-story house, with some fluid paths routed on the top story or top section 30*a* of the chamber 32, while other fluid paths routed on the bottom story or bottom section 30*b* of the chamber 32, with a piece of rigid plastic 30*c* separating the top and bottom story, and strategically placed through holes 30*d* connecting the two stories or sections. Each pump chamber 32 has holes 30*d* to allow fluid to be routed to or from the top 30a or bottom 30*b* of the chambers, depending on the fluid source. The drain line DL is routed to the top section 30*a* such that air, when partially purged, will exit to the drain. The patient line P is routed to the bottom section 30*b* to avoid delivery of air when the pump chamber's contents are partially delivered to the patient. In this manner, the cassette's pump chambers 32 can hold a certain volume of air. The volume of each pump chamber 32 is larger than the holdup volume of the tubing going from the cassette 30 to the admix bag 114 (FIG. 1). By doing so, the pump chamber 32 is able to draw in the entire contents of the tubing and some additional fluid from the admix bag 114, agitate it in the pump chamber 32, and deliver it back to the admix bag so as to ensure that the contents of the fluid in the admix bag's tubing is substantially the same concentration as the contents within the admix bag itself. In addition, if additional fluid mixing is needed, a piezoelectric shaking mechanism (not shown) may be incorporated into the top platform 11*a* of the device housing unit 11 holding the admix bag for further agitation to ensure uniform fluid concentrations throughout the admix bag.

The APD disposable cassette 30 utilizes multiple valves 31, as referred to as volcano valves, to control fluid routing to and from each of the following 9 sources: Patient, Drain, Admix Bag, Sterilized Water, Dextrose Bag Concentration A, Dextrose Bag Concentration B, Saline/Potassium Bag, Buffer Bag, and Last Fill Bag. The Saline Bag may consist of normal saline (0.9%) or hypertonic saline (3% or 5%). The Potassium Bag may consist of highly concentrated potassium chloride in water for injection, potassium chloride in normal saline (0.9%), or potassium chloride in 5% dextrose and saline, all currently commercially available. All sources listed as bags could alternatively be lyophilized powders in vials or similar containers. The powders may be reconstituted by the APD device by routing sterilized water to the vial or container, then drawing from the vial or container prior to delivery.

Figure 4:
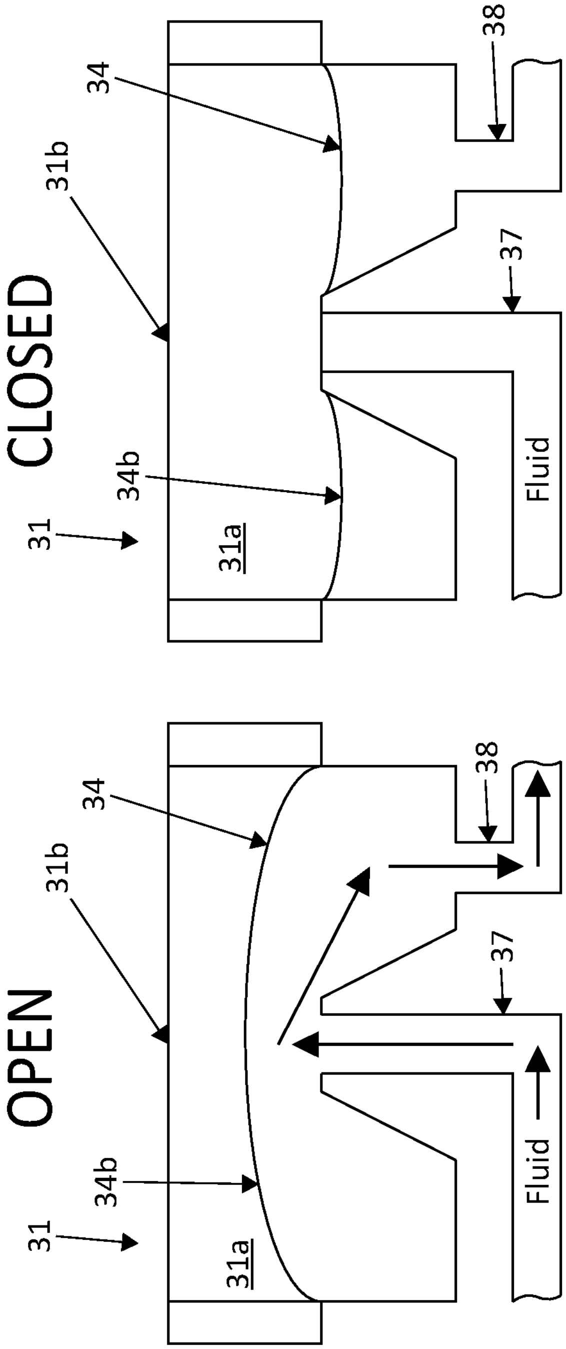
FIG. 4 illustrates the operation of a disposable cassette volcano valve utilized in the automated peritoneal dialysis (APD) device of the present disclosure.

FIG. 4 illustrates the operation of a disposable set volcano valve 31 utilized in the automated peritoneal dialysis (APD) cassette 30 of the present disclosure. This figure depicts a cross-sectional view of a volcano valve 31, with the adjacent air chamber 31*a* above each volcano valve. A hole 31*b* at the top of the air chamber 31*a* is connected to an air source (positive or vacuum pressure) through the pneumatic tubing 18 described earlier. Through operation of the pneumatic manifold 16, the flexible sheeting 34 is drawn away from the top of the volcano valve 31 when negative air pressure (1.5 to 5 psi vacuum) is applied, forming a dome 34*a* in the flexible sheeting as shown on the left on the OPEN side. This opens the pathway 37 to allow fluid to continue up through the volcano valve 31, over to the right, and down to the next fluid pathway 38. When positive pressure (7 to 8 psi) is applied, the flexible sheeting 34 is blown onto the surface of the volcano valve 31 in a concave 34*b*, as shown on the right CLOSED side. This closes the valve 31 such that fluid is not permitted to continue to travel to the next fluid pathway 38, similar to applying one's finger on the top of a drinking straw. Other cassette valve technologies could be used in alternative embodiments, such as a solenoid valve plunger protruding to bend flexible sheeting to block the flow path.

Figure 5:
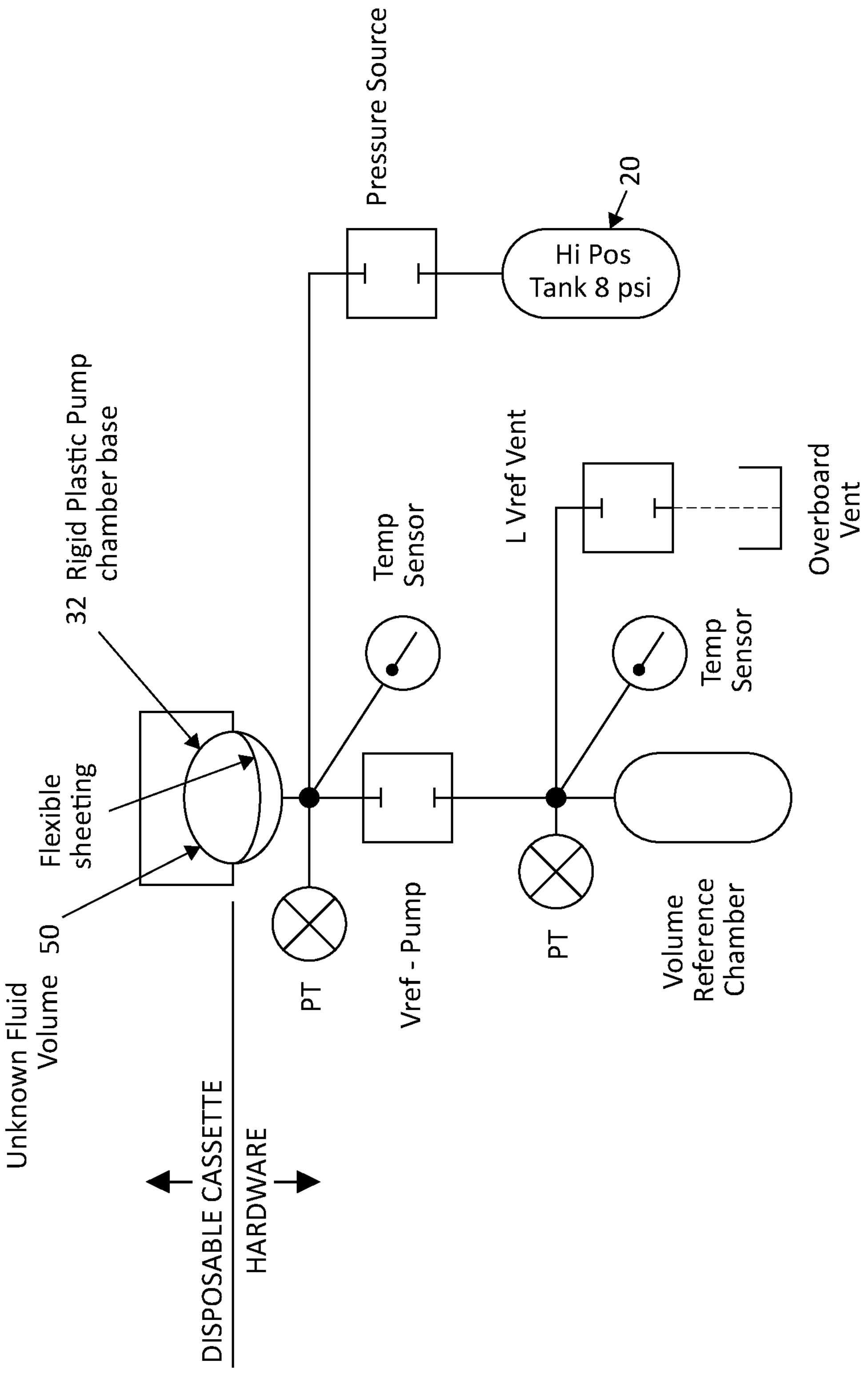
FIG. 5 illustrates a schematic of operation of the automated peritoneal dialysis (APD) device using the Ideal Gas Law to measure the unknown volume of fluid in one or more disposable cassette pump chambers. The temperature sensors shown may be combined with the respective pressure transducers if temperature-compensated pressure transducers are used.

As shown in the schematic of FIG. 5, in operation, the automated peritoneal dialysis (APD) device 10 utilizes a measurement system using the Ideal Gas Law to measure the unknown volume of fluid in one or more disposable cassette 30 pump chambers 32 by measuring the pressure on the hardware or pneumatic side of the pump chamber and pressures in a reference chamber with a known calibrated volume. PT designates "pressure transducer". A valve is shown between the disposable side and the volume reference chamber side, to allow air pressure from one side to transfer to the other side. Another valve connected to a vent is used to vent out pressure in between each measurement. A High Positive Tank 20 is held at a constant 8 psi as a pressure accumulator to pressurize the volume reference (Vref) chamber as needed. When the volume reference chamber requires 8 psi air, the Pressure Source valve allows air to transfer from the tank to the Vref chamber. Pressure transducers measure the pressure within a confined hardware pump chamber region just outside of the disposable tubing set's flexible pump chamber. A bolus of fluid 50 with an initially unknown volume is shown inside of the disposable cassette's pump chamber 32, shown in the shaded region. It is trapped in place by the disposable cassette's volcano valves (not shown). Temperature sensors measure the temperature of the hardware air chamber just outside the disposable pump chamber and the Vref chamber.

Figure 6:
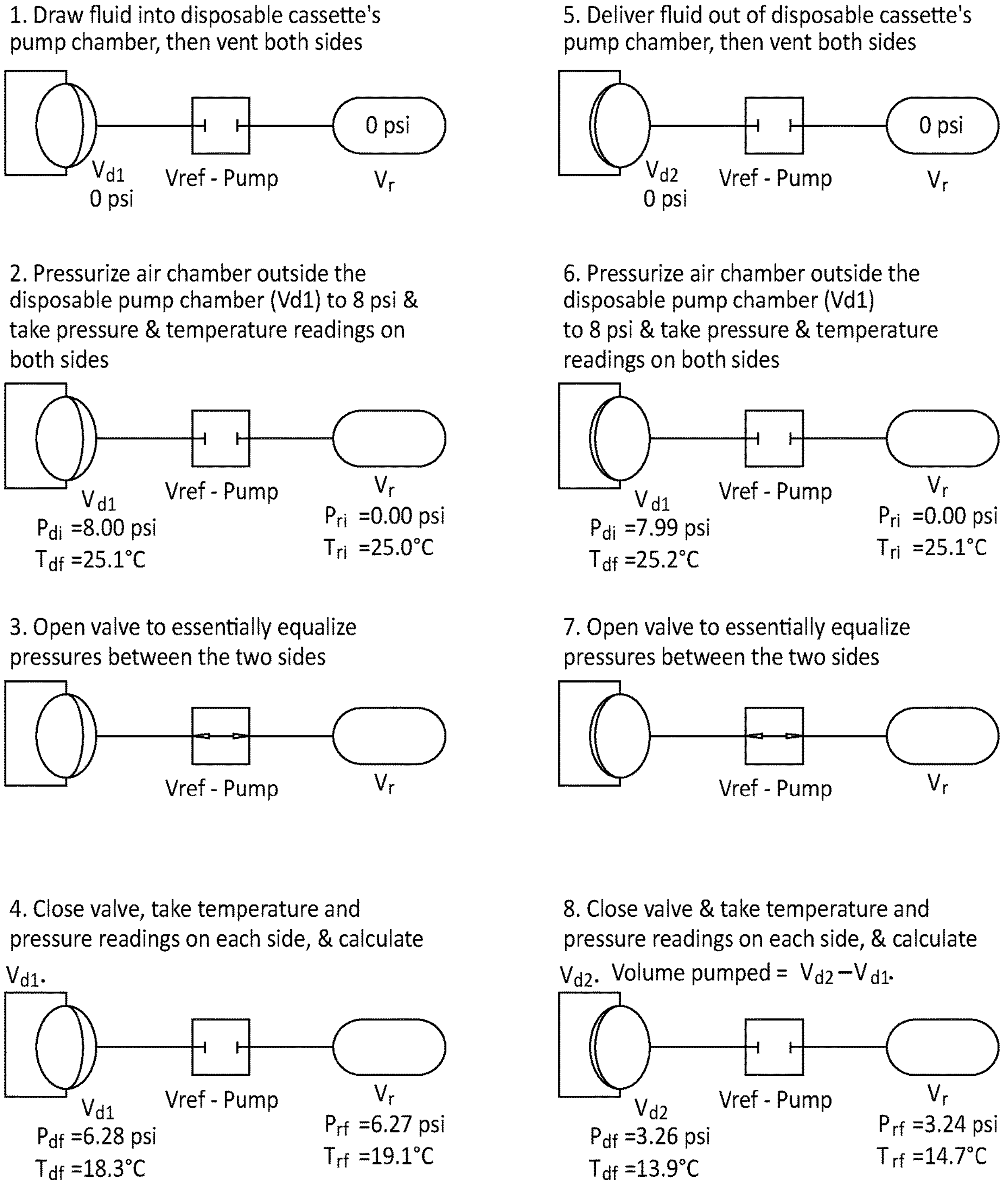
FIG. 6 illustrates a schematic of the sequence of steps that must be taken in order to measure the volume of air on the pneumatic side of the disposable pump chamber of the APD device of the present disclosure, both before and after a bolus of fluid has been delivered from the pump chamber.

FIG. 6 illustrates shows the series of steps that must be taken, in this sequence, in order to measure the volume of air on the hardware or pneumatic side of the disposable pump chamber 32, both before and after a bolus of fluid 50 has been delivered from the pump chamber. Each of the 8 mini-figures shows a disposable set with fluid inside it, an air chamber on the hardware side of the disposable pump chamber with air volume $V_d$, a pneumatic solenoid valve, Vref—Pump, and a volume reference chamber with a known air volume $V_r$. The left side shows the sequence of steps to calculate the air volume $V_{d1}$ in the 1st state (with fluid in the disposable pump chamber), while the right side shows the sequence of steps to calculate the air volume $V_{d2}$ in the 2nd state (with fluid having been delivered from the pump chamber to its intended destination.) In this manner, by subtracting the before and after air volumes from each other ($|V_{d2}-V_{d1}|$), one can calculate the volume of fluid pumped from the disposable pump chamber.

The governing equations are shown below:

$$PV = nRT \text{ (Ideal Gas Law), or rearranging, } n = PV/RT$$

There are two sides containing air, the disposables side, designated as "d", and the reference chamber side, designated as "r". Each side has an initial state, designated by "i", and a final state after pressures between the two sides have been essentially equalized, designated by "f".

The number of moles of air on the disposables side in the initial state is calculated as:

$$n_{di} = \frac{P_{di} V_d}{RT_{di}}$$

where $V_d$ is the unknown volume of the disposables side to calculate.

The number of moles of air on the reference chamber side in the initial state is calculated as:

$$n_{ri} = \frac{P_{ri} V_r}{RT_{di}}$$

where $V_r$ is the volume of air in the reference chamber, which is a known, fixed value.

The number of moles of air on the disposables side in the final state is calculated as:

$$n_{df} = \frac{P_{df} V_d}{RT_{df}}$$

The number of moles of air on the reference chamber side in the final state is calculated as:

$$n_{rf} = \frac{P_{rf} V_r}{RT_{df}}$$

Since the total number of moles of both sides put together remains constant (air is simply shuffled from one side to the other as pressure is released from the reference chamber to the disposables side), the formula is the following:

$$n_{di} + n_{ri} = n_{df} + n_{rf}$$

Therefore, by substitution, the calculation is the following:

$$\frac{P_{di} V_d}{RT_{di}} + \frac{P_{ri} V_r}{RT_{di}} = \frac{P_{df} V_d}{RT_{df}} + \frac{P_{rf} V_r}{RT_{df}}$$

The R term cancels out. Rearranging, the calculation is:

$$V_d\left(\frac{P_{di}}{T_{di}} - \frac{P_{df}}{T_{df}}\right) = V_r\left(\frac{P_{rf}}{T_{rf}} - \frac{P_{ri}}{T_{ri}}\right)$$

Solving for Vd, the calculation is:

$$V_d = V_r\left[\frac{\left(\frac{P_{rf}}{T_{rf}} - \frac{P_{ri}}{T_{ri}}\right)}{\left(\frac{P_{di}}{T_{di}} - \frac{P_{df}}{T_{df}}\right)}\right]$$

This is the equation that governs the volume calculations if using temperature measurement.

However, if temperature of the reference chamber and the disposables side are held in thermal contact with each other such that they are essentially constant, the equation simplifies as:

$$V_d = V_r\left(\frac{P_{rf} - P_{ri}}{P_{di} - P_{df}}\right)$$

Additional temperature compensation via direct temperature measurement of the volume reference chamber and/or pump chamber may be added to increase volumetric accuracy, since the Ideal Gas Law calculates volume as a function of pressure and temperature as described above.

Alternatively, the temperature of the volume reference chamber may be held quasi-constant at or near body temperature by placing the volume reference chamber in thermal contact with the cassette's pump chamber and/or by including a thermally conductive wire mesh material inside the volume reference chamber to provide a high degree of surface area for quickly stabilizing the gas temperature within the volume reference chamber even after a rapid temperature excursion due to rapid pressure changes within the reference chamber. In this alternative, no temperature measurement is necessary.

Figure 7:
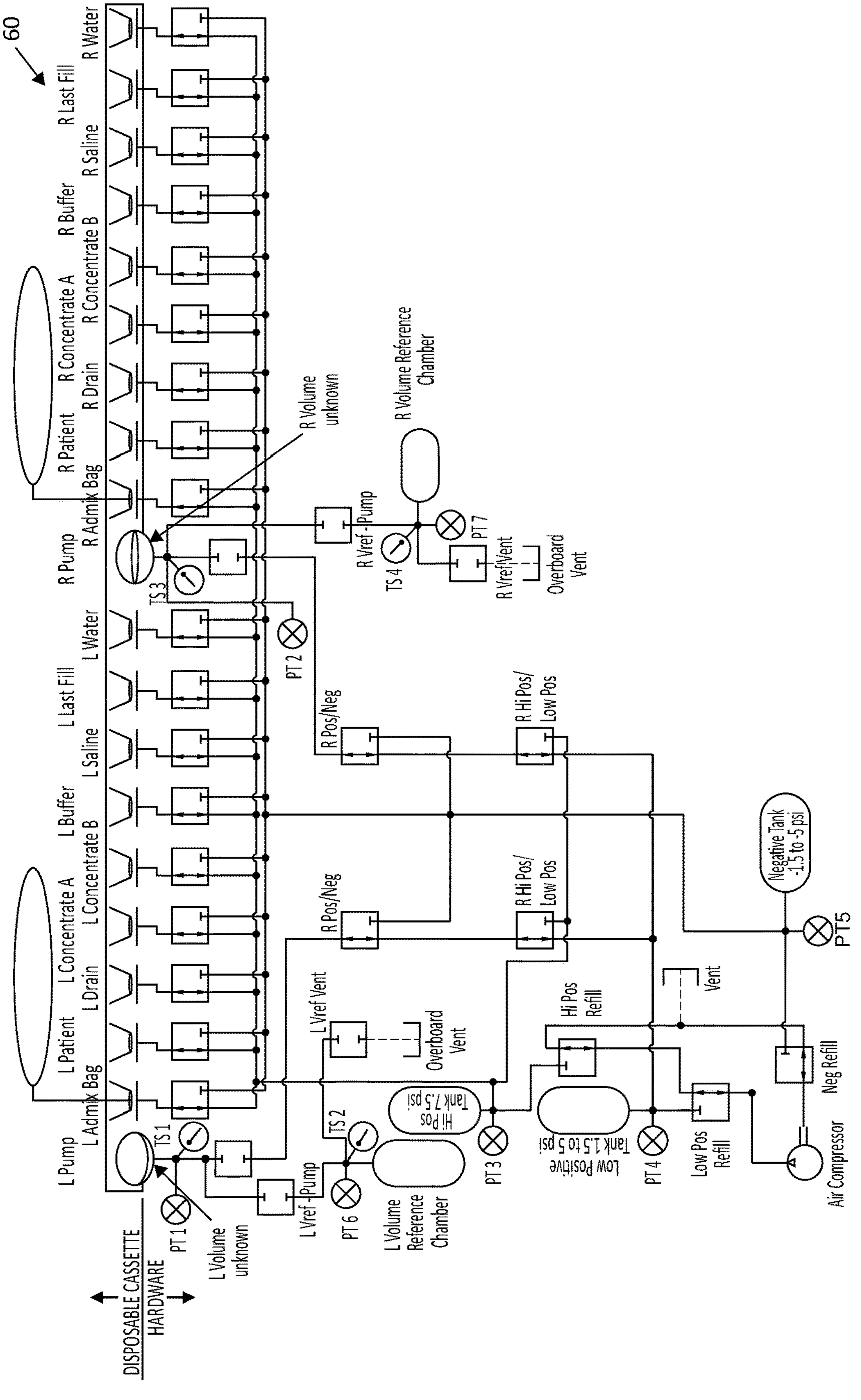
FIG. 7 illustrates the pneumatic schematic of the automated peritoneal dialysis (APD) device of the present disclosure.

FIG. 7 illustrates the pneumatic schematic operation 60 of the automated peritoneal dialysis (APD) device of the present disclosure. The top horizontal portion shows the two pump chambers (left and right) and 18 volcano valves in the disposable tubing set. Each pump chamber has its pressure measured by a pressure transducer, as shown in PT 1 and PT 2, and by temperature sensors, TS 1 and TS 3. Each pump chamber is capable of pumping fluid to or from the following 9 sources: Admix Bag, Patient, Drain, Dextrose Concentrate A, Dextrose Concentrate B, Buffer, Saline/Potassium, Last Fill, and Sterilized Water. A 3-way pneumatic solenoid valve is used to route either positive or negative air pressure to the outside surface of each of the 18 disposable set volcano valves. Each pump chamber is pressurized via a 2-way normally closed solenoid valve, shown just underneath each pump chamber. A Vref—pump solenoid valve is found for each pump chamber to allow air to communicate between the volume reference chamber and the pump chamber. Each of the two volume reference chambers has its own pressure transducer and temperature sensor, as shown with PT 6, TS 2, PT 7, and TS 4. Each volume reference chamber also has its own vent solenoid valve. A series of pressure tanks, or accumulators, is shown in the High Positive (Hi-Pos) Tank, the Low Positive Tank, and the Negative Tank, with each tank's pressure measured by a pressure transducer as shown in PT 3, PT 4, and PT 5. Also, each tank is allowed to either continue to be pressurized or be held at its current pressure via 3-way "Refill" solenoid valves. When the pump is not pressurizing (or adding vacuum pressure to) a tank, the air from the pump is sent from the Refill valves to an overboard vent. Although the Overboard Vents are shown separately on the schematic, they could be combined into a single vent if desired. A 3-way Pos/Neg solenoid valve allows air to be routed to the pump chambers either from the one of the Positive Tanks or the Negative Tank. A 3-way Hi Pos/Low Pos solenoid valve allows air to be routed to the pump chambers either from the Hi Positive Tank or the Low Positive Tank.

In the past, clinicians have not been able to customize the sodium or potassium used in APD therapy. Clinicians currently have PC-based software tools to determine how to prescribe the dextrose concentration and dwell times in order to remove a certain volume of ultrafiltration, but they do not have any tools to help them prescribe the sodium concentration and dwell times in order to remove a certain quantity of sodium from the patient's bloodstream with each therapy. These existing prescription optimization tools have historically been based on kinetic modeling of solute transport across the peritoneum. The present disclosure further includes an easy-to-use therapy software that will aid clinicians in the selection of optimized sodium, potassium, and glucose concentrations based on a patient's specific health factors, so that clinicians will easily be able to use the present APD device for optimal patient outcomes.

Figure 8:
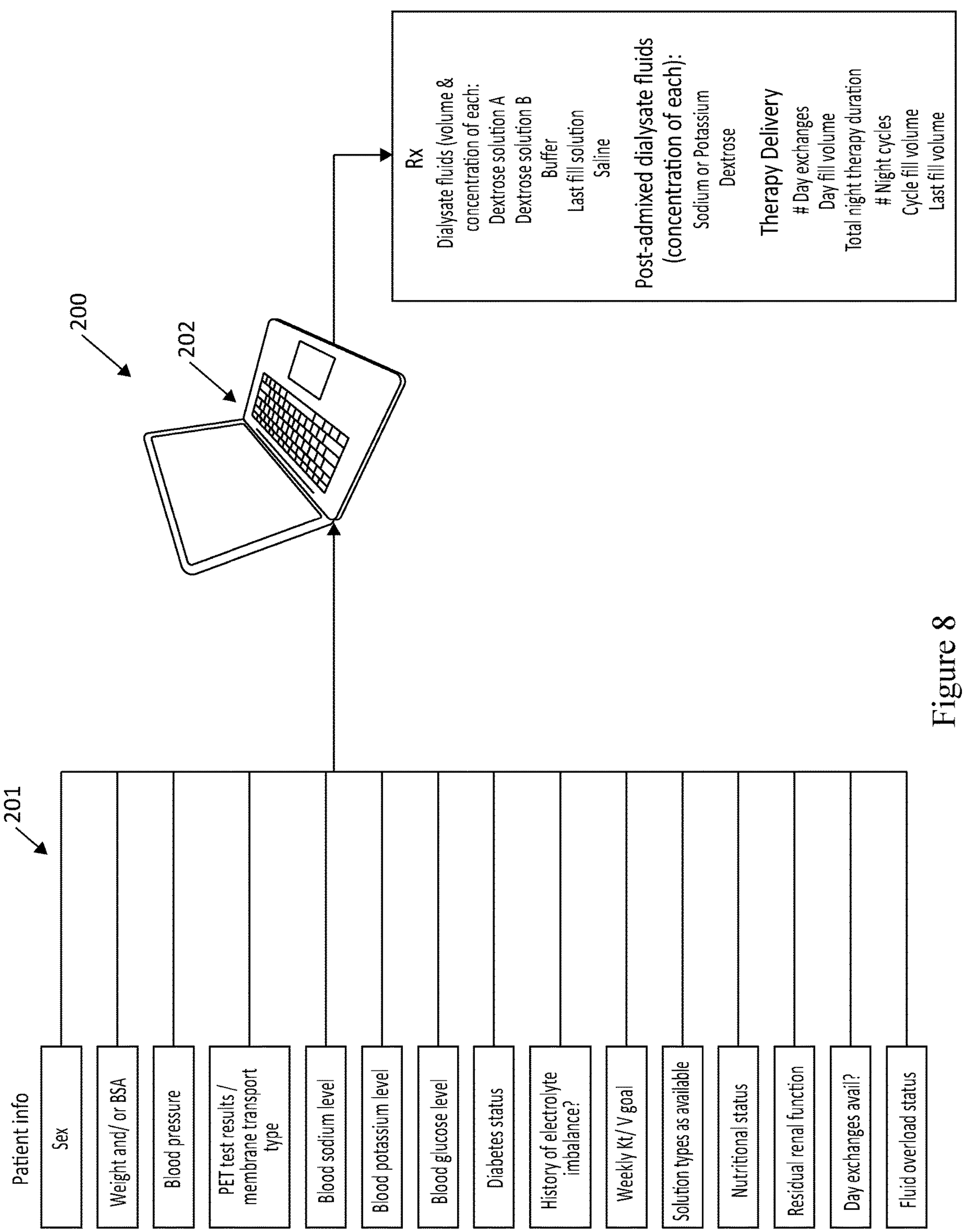
FIG. 8 illustrates a PC-based software application for calculating a set of prescription optimization parameters that may be used to automatically generate one or more prescriptions that meet the desired goals for optimizing blood sodium levels, blood potassium levels, minimizing dextrose exposure, and typical peritoneal dialysis parameters, such as ultrafiltration goals to achieve the desired toxin clearances utilizing the automated peritoneal dialysis (APD) device of the present disclosure.

As illustrated in FIG. 8, there is shown a PC-based software application 200 for calculating a set of prescription optimization parameters 201 that may be used to automatically generate one or more prescriptions that meet the desired goals for optimizing blood sodium levels, along with typical peritoneal dialysis parameters, such as ultrafiltration goals to achieve the desired toxin clearances utilizing the automated peritoneal dialysis (APD) device of the present disclosure. These parameters 201 can be manually input into the cycler via the cycler's user interface, or automatically transferred via wired or wireless communication from a clinician's PC 202 to the patient's cycler. Given that clinicians may not know how much sodium to remove from the patient, this prescription optimization software 200 is envisioned to automatically calculate the concentration of post-admixed sodium, based on certain input parameters including blood sodium levels. It is envisioned that the input concentrated saline may only come in a finite number of concentrations, such as 0.9%, 3%, or 5%. This software 200 could then take those inputs and generate the volume and concentration required from the input saline bag to admix with sterile water, Dextrose A, optional Dextrose B, and optional buffer solution to produce the desired output sodium and dextrose levels. Similar calculations could occur for tailoring other electrolytes or minerals, such as potassium, magnesium or calcium.

For example, the present APD device 10 and system 100 utilizes the PC-based software application 200 to estimate the amount of dextrose to deliver to the patient as a function of the sodium content. Since both dextrose and sodium are osmotic agents, if a patient is given a lower-than-normal sodium dialysate solution, the dextrose concentration must be adjusted upward in order to maintain the same equivalent osmotic gradient as a normal sodium (i.e. 132-134 mmol/l) dialysate solution would have had. An advantage of the present software application 200 is that the software will calculate the sodium (or potassium) concentration to deliver, based on the user-entered desired weekly or daily sodium removal (or potassium addition) target, along with the patient's physical characteristics 201 such as peritoneal transport type (High, High Average, Low Average, or Low), body surface area, and blood sodium (or potassium) concentration.

The software application 200 will also automatically calculate the concentration of dextrose and volume to deliver from each of the source containers, based on the sodium concentration and ultrafiltration (UF) targets, to achieve the same osmolality of the equivalent normal sodium (or potassium) concentration and normal dextrose concentration solution that would be needed to achieve those UF targets. This software application 200 could be installed on the clinician's PC 202 and/or be accessible via web browser.

The known 3-pore kinetic model of peritoneal dialysis may be used to estimate therapy outcomes based on the solution concentrations and patient's body characteristics. For example, the present software application 200 and/or the ADP device 10 programming screens will calculate the appropriate sodium removal or potassium addition prescription for an individual patient. As shown in FIG. 8, input parameters 201 will include some or all of the following: Sex, Weight, Body Surface Area, blood pressure, PET test results or membrane transport type (high, high-average, low-average, or low), serum sodium level, serum potassium level, serum glucose level, diabetes status, history of electrolyte imbalance (e.g. hyper/hyponatremia or hyper/hypokalemia), weekly Kt/V goal, icodextrin and/or biocompatible solutions availability, nutritional status, residual renal function, availability of using both day and night exchanges vs. only night exchanges, fluid overload status. Outputs will define the number of day and night cycles, cycle fill volume, therapy duration, sodium concentration, potassium concentration, and dextrose concentration, as well as the predicted nightly sodium removal and/or potassium addition in milligrams. This will allow the user to associate their dietary intake with the sodium removal capabilities of their peritoneal dialysis prescription. The prescription can then be adjusted as needed, based on approximately monthly blood draws when the patient visits their nephrology clinic, to ensure electrolyte removal/addition targets and fluid removal (ultrafiltration targets are being achieved.

Yet another advantage in utilizing the present software application 200 is that the final clinician-approved dialysis prescription can then be remotely downloaded to the APD device 10 such that the patient does not have to manually enter each of the prescription parameters on the APD device's user interface. This prescription could be adjusted regularly as needed, based on new blood measurements that occur approximately once per month, using the same input parameters 201 shown in FIG. 8. Alternatively, if sodium, potassium, and/or glucose measurement are available within the home, either from the patient's blood or from the spent effluent, the prescription could be updated daily if desired, for near real-time adjustment. This could further reduce the likelihood of hyponatremia or hypernatremia or other electrolyte imbalance.

Operation and Examples

In operation, and by way of example, the present APD device 10 and system 100 envisions two concentrated dialysate dextrose solutions, Dextrose A and Dextrose B, intended to be mixed in various proportions to produce an intermediate dextrose concentration after dilution with sterile water, hypertonic saline, and buffer solution. Dextrose A is intended to produce 1.0% dextrose solution at 100 mEq/l after dilution, while Dextrose B is intended to produce 4.5% dextrose at 100 mEq/l after water dilution and before any hypertonic saline addition. Both Dextrose A and Dextrose B would contain 30% Dextrose Hydrous.

Dextrose A, in one embodiment, would contain the following composition per 100 ml: Dextrose Hydrous 30.0 g, Calcium Chloride Dihydrate ($CaCl_2 \cdot 2H_2O$) 552.0 mg, Magnesium Chloride Hexahydrate ($MgCl_2 \cdot 6H_2O$) 153.0 mg.

Dextrose B, in one embodiment, would contain the following composition per 100 ml: Dextrose Hydrous 30.0 g, Calcium Chloride Dihydrate ($CaCl_2 \cdot 2H_2O$) 122.7 mg, Magnesium Chloride Hexahydrate ($MgCl_2 \cdot 6H_2O$) 34.0 mg.

The Buffer Solution, in one embodiment, would contain the following composition per 100 ml: Sodium Chloride 7014 mg, Sodium Lactate ($C_3H_5NaO_3$) 3360 mg, Sodium Bicarbonate ($NaHCO_3$) 4200 mg.

A 200 ml container of Dextrose A, after dilution with a 300 ml container of Buffer Solution and 5500 ml of sterile water, would yield the following solution composition per 100 ml: Dextrose Hydrous 1.0 g, Sodium Chloride (NaCl) 350.7 mg, Sodium Lactate ($C_3H_5NaO_3$) 168 mg, Calcium Chloride Dihydrate ($CaCl_2 \cdot 2H_2O$) 18.4 mg, Magnesium Chloride Hexahydrate ($MgCl_2.6H_2O$) 5.10 mg, Sodium Bicarbonate ($NaHCO_3$) 210 mg.

A 900 ml container of Dextrose B, after dilution with a 300 ml container of Buffer Solution and 4800 ml of sterile water, would yield the following solution composition/100 ml: Dextrose Hydrous 4.5 g, Sodium Chloride (NaCl) 350.7 mg, Sodium Lactate ($C_3H_5NaO_3$) 168 mg, Calcium Chloride Dihydrate ($CaCl_2 \cdot 2H_2O$) 18.4 mg, Magnesium Chloride Hexahydrate ($MgCl_2.6H_2O$) 5.10 mg, Sodium Bicarbonate ($NaHCO_3$) 210 mg.

The admixing of Dextrose A, Dextrose B, Buffer Solution, and Sterile Water could be augmented by further admixing hypertonic saline in one embodiment to increase the sodium concentration from 100 mEq/l to any intermediate value up to and including 170 mEq/l. The volume of sterile water used for dilution is reduced by the corresponding amount of hypertonic saline added. As an example if a dextrose concentration of 2.0% and a sodium concentration of 110 mEq/l is desired (rather than 100 mEq/l), an additional 117 ml of 3% hypertonic saline would be added to 143 ml of Dextrose A, 257 ml of Dextrose B, and 300 ml of Buffer Solution, and 5183 ml of sterile water to create 6000 ml of admixed solution.

In another example, the present APD device 10 utilizes similar ultra-low sodium solutions as the previous paragraph, except without the use of buffer solutions. Again, both Dextrose A and Dextrose B would contain 30% Dextrose Hydrous.

Dextrose A, in one embodiment, would contain the following composition per 100 ml: Dextrose Hydrous 30.0 g, Sodium Chloride 10523 mg, Calcium Chloride Dihydrate ($CaCl_2 \cdot 2H_2O$) 552.0 mg, Magnesium Chloride Hexahydrate ($MgCl_2 \cdot 6H_2O$) 153.0 mg.

Dextrose B, in one embodiment, would contain the following composition per 100 ml: Dextrose Hydrous 30.0 g, Sodium Chloride 2339 mg, Calcium Chloride Dihydrate ($CaCl_2 \cdot 2H_2O$) 122.7 mg, Magnesium Chloride Hexahydrate ($MgCl_2.6H_2O$) 34.0 mg.

A 200 ml container of Dextrose A, after dilution with 5800 ml of sterile water, would yield the following solution composition per 100 ml: Dextrose Hydrous 1.0 g, Sodium Chloride (NaCl) 350.8 mg, Sodium Lactate ($C_3H_5NaO_3$) 448 mg, Calcium Chloride Dihydrate ($CaCl_2 \cdot 2H_2O$) 18.4 mg, Magnesium Chloride Hexahydrate ($MgCl_2.6H_2O$) 5.10 mg.

A 900 ml container of Dextrose B, after dilution with 4100 ml of sterile water, would yield the following solution composition per 100 ml: Dextrose Hydrous 4.5 g, Sodium Chloride (NaCl) 350.8 mg, Sodium Lactate ($C_3H_5NaO_3$) 448 mg, Calcium Chloride Dihydrate ($(CaCl_2) \cdot 2H_2O$) 18.4 mg, Magnesium Chloride Hexahydrate ($MgCl_2 \cdot 6H_2O$) 5.10 mg.

The admixing of Dextrose A, Dextrose B, and Sterile Water could be augmented by further admixing hypertonic saline in one embodiment to increase the sodium concentration from 100 mEq/l to any intermediate value up to and including 170 mEq/l. The volume of sterile water used for dilution is reduced by the corresponding amount of hypertonic saline added. As an example if a dextrose concentration of 2.0% and a sodium concentration of 110 mEq/l is desired (rather than 100 mEq/l), an additional 117 ml of 3% hypertonic saline would be added to 143 ml of Dextrose A, 257 ml of Dextrose B, and 5483 ml of sterile water to create 6000 ml of admixed solution.

It should be noted that various changes and modifications to the presently preferred embodiments described herein will be apparent to those skilled in the art. Such changes and modifications may be made without departing from the spirit and scope of the present invention and without diminishing its attendant advantages.

The invention claimed is:

1. A method for determining an appropriate peritoneal dialysis prescription tailored to meet treatment needs of a patient, the method comprising the steps of;

providing an input computing device configured for receiving health parameters of the patient;

inputting the patient health parameters into the computing device;

providing at least one bag containing an electrolyte solution;

calculating a concentration of electrolytes from the electrolyte solution for a treatment solution based on the patient health parameters at a time of treatment;

inputting the calculated concentration of electrolytes from the electrolyte solution into an automated peritoneal dialysis (APD) device;

mixing the concentration of electrolytes in the APD device into the treatment solution suitable for administration to the patient;

administering the treatment solution to the patient, wherein the method further includes removing a determined quantity of sodium from the patient's bloodstream at the time of each treatment based on the patient health parameters.

2. The method of claim 1, wherein the electrolytes are at least one of sodium or potassium.

3. The method of claim 1, wherein the method further includes providing a bag containing a dextrose solution.

4. The method of claim 3, wherein the method further includes using the input computing device to calculate an amount of a dextrose concentration to deliver to the patient based on a sodium concentration.

5. The method of claim 4, wherein the input computing device automatically adjusts the dextrose concentration higher when a lower sodium concentration is selected.

6. The method of claim 5, wherein the method further includes maintaining an osmotic gradient by adjusting the dextrose concentration as a function of the sodium concentration.

7. The method of claim 3, wherein the method further includes using the input computing device to calculate a dextrose concentration to deliver to the patient based on a potassium concentration.

8. The method of claim 7, wherein the input computing device automatically adjusts the dextrose concentration lower when a higher potassium concentration is selected.

9. The method of claim 8, wherein the method further includes maintaining an osmotic gradient by adjusting the dextrose concentration as a function of the potassium concentration.

10. A method for determining an appropriate peritoneal dialysis prescription tailored to meet treatment needs of a patient, the method comprising the steps of:

providing an input computing device configured for receiving health parameters of the patient;

inputting the patient health parameters into the computing device;

providing at least one bag containing an electrolyte solution;

calculating a concentration of electrolytes from the electrolyte solution for a treatment solution based on the patient health parameters at a time of treatment;

inputting the calculated concentration of electrolytes from the electrolyte solution into an automated peritoneal dialysis (APD) device;

mixing the concentration of electrolytes in the APD device into the treatment solution suitable for administration to the patient;

administering the treatment solution to the patient, wherein the method includes adding a determined quantity of potassium to the patient's bloodstream at the time of each treatment based on the patient health parameters.

* * * * *